United States Patent
Garlock et al.

(10) Patent No.: US 10,213,219 B2
(45) Date of Patent: Feb. 26, 2019

(54) TARGETING GUIDE ASSEMBLY

(71) Applicant: ARTHREX, INC., Naples, FL (US)

(72) Inventors: Adam Garlock, Bonita Springs, FL (US); Ronald J. Choinski, Fort Myers Beach, FL (US); Jerome Gulvas, Bonita Springs, FL (US); Zachary Day, Naples, FL (US)

(73) Assignee: ARTHREX, INC., Naples, FL (US)

( * ) Notice: Subject to any disclaimer, the term of this patent is extended or adjusted under 35 U.S.C. 154(b) by 331 days.

(21) Appl. No.: 14/740,631

(22) Filed: Jun. 16, 2015

(65) Prior Publication Data

US 2016/0367270 A1    Dec. 22, 2016

(51) Int. Cl.
| | | |
|---|---|---|
| *A61B 17/17* | (2006.01) | |
| *A61B 17/88* | (2006.01) | |
| *A61B 90/11* | (2016.01) | |
| *A61B 17/90* | (2006.01) | |

(52) U.S. Cl.
CPC .......... *A61B 17/1739* (2013.01); *A61B 17/88* (2013.01); *A61B 90/11* (2016.02); *A61B 17/1775* (2016.11); *A61B 2017/90* (2013.01)

(58) Field of Classification Search
CPC . A61B 17/1739; A61B 17/88; A61B 17/1775; A61B 2017/90; A61B 90/11
USPC .. 606/92–96, 86 R, 98, 80, 87–89, 148, 228
See application file for complete search history.

(56) References Cited

U.S. PATENT DOCUMENTS

| | | | | |
|---|---|---|---|---|
| 4,865,025 | A * | 9/1989 | Buzzi ................. | A61B 17/1703 606/96 |
| 5,766,179 | A * | 6/1998 | Faccioli ............ | A61B 17/1725 606/96 |
| 6,342,056 | B1 * | 1/2002 | Mac-Thiong ...... | A61B 17/1757 606/103 |
| 7,842,042 | B2 | 11/2010 | Reay-Young et al. | |
| 8,277,458 | B2 * | 10/2012 | Schneider .......... | A61B 17/0401 606/86 R |
| 8,343,199 | B2 | 1/2013 | Tyber et al. | |
| 8,449,552 | B2 | 5/2013 | Sanders | |
| 8,523,872 | B2 | 9/2013 | Ek | |
| 8,740,913 | B2 | 6/2014 | Schneider | |
| 8,951,261 | B2 | 2/2015 | Sharkey et al. | |
| 8,986,316 | B1 * | 3/2015 | Jordan ............... | A61B 17/1714 606/96 |
| 9,474,552 | B2 * | 10/2016 | Barnett ............. | A61B 17/6416 |
| 2012/0253354 | A1 | 10/2012 | Arlettaz et al. | |
| 2013/0035561 | A1 | 2/2013 | Sharkey et al. | |
| 2013/0090662 | A1 | 4/2013 | Hanson et al. | |

(Continued)

OTHER PUBLICATIONS

International Search Report and Written Opinion for PCT Application No. PCT/US2015/061495, dated Feb. 18, 2016.

(Continued)

*Primary Examiner* — Pedro Philogene
(74) *Attorney, Agent, or Firm* — Carlson, Gaskey & Olds

(57) ABSTRACT

This disclosure relates to a targeting guide assembly for positioning a surgical instrument. The targeting guide assembly is used to accurately place a surgical instrument for establishing a precise path for subsequent screw placement, retrograde drilling, etc. A targeting guide assembly according to an exemplary aspect of the present disclosure includes, among other things, a first bracket, a second bracket rotatable relative to the first bracket and a cannula guide body movable within a slot of the first bracket.

21 Claims, 10 Drawing Sheets

(56) References Cited

U.S. PATENT DOCUMENTS

2014/0024927 A1\* 1/2014 Piferi ................ A61B 17/1703
600/417
2014/0228848 A1 8/2014 Torrie et al.

OTHER PUBLICATIONS

International Preliminary Report on Patentability for PCT Application No. PCT/US2015/061495, dated Dec. 28, 2017.

\* cited by examiner

SECTION A-A

TARGETING GUIDE ASSEMBLY

BACKGROUND

This disclosure relates to a targeting guide assembly for accurately positioning surgical instruments.

Arthroscopic procedures are commonly performed to diagnose and treat problems in joints, such as the ankle, knee, shoulder, or hip joint. Ligament reconstruction, bone resurfacing and joint replacement are several examples of procedures that may be performed arthroscopically by working through a series of relatively small portals. It may be difficult to accurately position the surgical instrumentation needed to perform a specific procedure through the arthroscopic portals. For example, it can be difficult to control the trajectory of guidewires being placed into the joint to facilitate proper placement of drills, screws, or other surgical instruments.

SUMMARY

This disclosure relates to a targeting guide assembly for positioning a surgical instrument. The targeting guide assembly is used to accurately place a surgical instrument for establishing a precise path for subsequent screw placement, retrograde drilling, etc.

A targeting guide assembly according to an exemplary aspect of the present disclosure includes, among other things, a first bracket, a second bracket rotatable relative to the first bracket and a cannula guide body movable within a slot of the first bracket.

A surgical method according to another exemplary aspect of the present disclosure includes, among other things, positioning an indicator probe of a targeting guide assembly at a first location of a joint, positioning a cannula of the targeting guide assembly at a second location relative to the joint such that the cannula is aligned to establish a desired trajectory toward the indicator probe, and inserting a surgical instrument through the cannula along the desired trajectory. The step of positioning the cannula includes moving a cannula guide body in a slot of the targeting guide assembly.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes a targeting guide assembly for use during surgical procedures. The targeting guide assembly is utilized to accurately position guidewires, drills or other surgical instruments for a subsequent screw placement, drilling procedure, or any other procedure where precise surgical instrument and/or implant placement is desired.

In some embodiments, the targeting guide assembly includes a first bracket, a second bracket and a cannula guide body. The second bracket is rotatable with respect to the first bracket. The first bracket includes a slot, and the cannula guide body is moveable within the slot, such as along a curvilinear path. In other embodiments, a cannula may be ratcheted within the cannula guide body to adjust its positioning relative to a joint. These and other features are described in detail in the following paragraphs of this detailed description.

Figure 1:
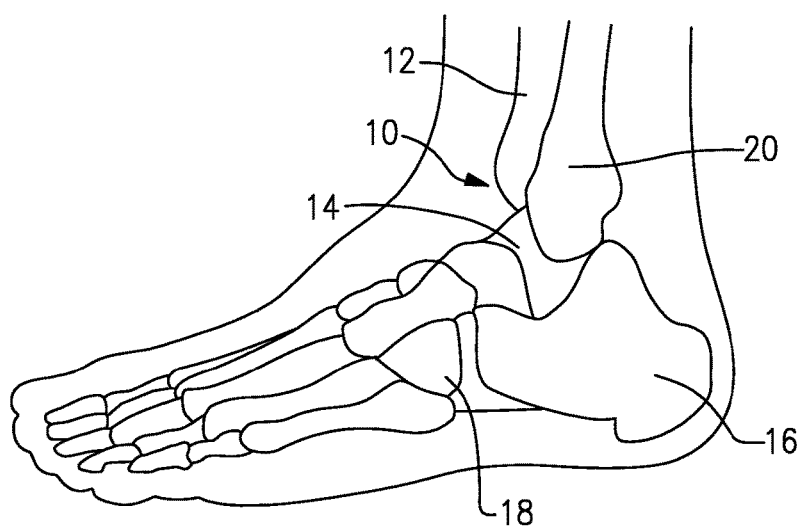
FIG. 1 illustrates a joint of a human musculoskeletal system.

FIG. 1 illustrates a joint 10 of the human musculoskeletal system. In a non-limiting embodiment, the joint 10 is an ankle joint; however, the joint 10 could be any joint of the human musculoskeletal system. The exemplary ankle joint includes a tibia 12 and a talus 14 that supports the tibia 12. Other bones of the ankle joint include the calcaneus 16, the cuboid 18 and the fibula 20.

Certain aspects of the joint 10 may be damaged or may deteriorate to such a degree that surgery is required to alleviate pain and stabilize the joint 10. This disclosure describes a targeting guide assembly that may be used during such surgical procedures for accurate positioning and placement of a surgical instrument. Although the targeting guide assembly of this disclosure is often illustrated and described with reference to an ankle joint, this disclosure is not limited to such an embodiment. In other words, the surgical tools and techniques described herein may be used to achieve accurate placement of a surgical instrument within any joint of the human musculoskeletal system.

Figure 2A:
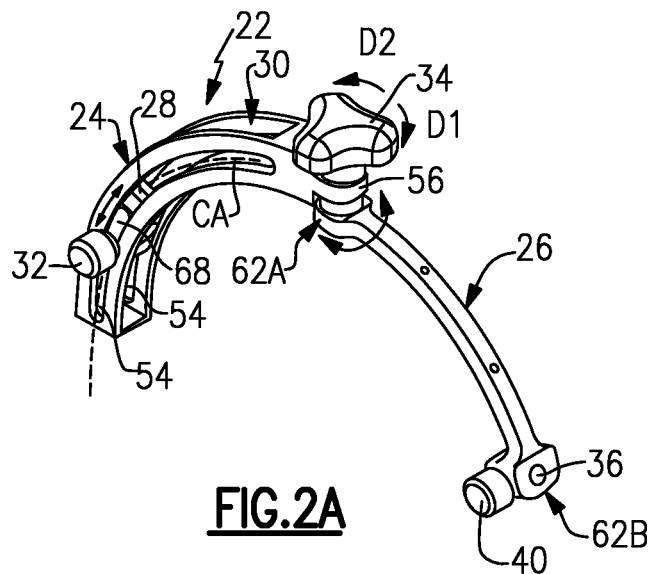
FIGS. 2A and 2B illustrate a targeting guide assembly for positioning a surgical instrument during a surgical procedure.
Figure 2B:
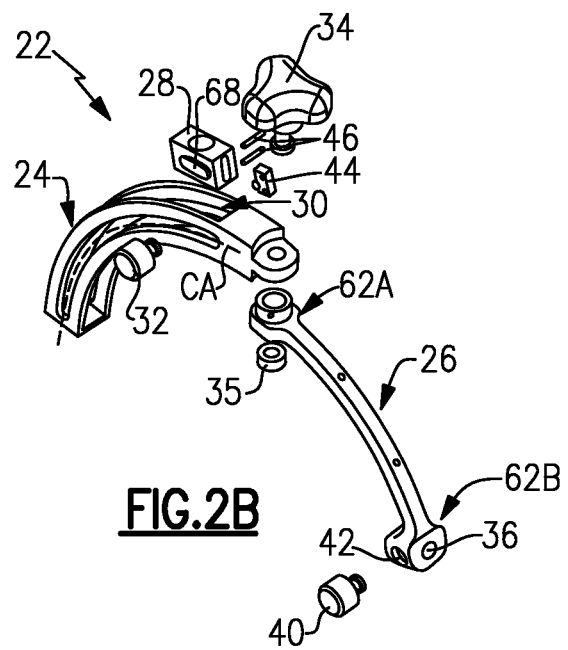

FIGS. 2A and 2B illustrate an exemplary targeting guide assembly 22. FIG. 2A is an isometric view, whereas FIG. 2B is an exploded view of the targeting guide assembly 22. The targeting guide assembly 22 is an orthopedic surgical device that may be part of a surgical instrumentation set or kit for preparing a joint for a surgical procedure. In one non-limiting embodiment, the targeting guide assembly 22 is configured to accurately position a guidewire or other surgical instrument within a joint to prepare the joint for a subsequent fusion procedure, screw placement procedure, drilling procedure or other surgical procedure.

The targeting guide assembly 22 may include a first bracket 24, a second bracket 26 and a cannula guide body 28. In one non-limiting embodiment, the cannula guide body 28 is mounted for movement within a slot 30 of the first bracket 24. The slot 30 may extend along a curved axis CA, and thus the cannula guide body 28 is movable along a curvilinear path defined by the slot 30 to locate a cannula (shown as reference feature 25 in FIGS. 7 and 8) at a desired position relative to a joint.

A ratchet 44 may be mounted inside the cannula guide body 28. In one non-limiting embodiment, the ratchet 44 is mounted to the cannula guide body 28 using one or more pins 46 (best shown in FIG. 2B). The ratchet 44 is configured to articulate relative to an outer surface of the cannula 25 to adjust the positioning of the cannula 25 within the cannula guide body 28, as further discussed below with reference to FIG. 7.

A guide knob 32 may be secured to the cannula guide body 28. The guide knob 32 protrudes outwardly from the slot 30 in a direction away from the first bracket 24. The guide knob 32 may be gripped for maneuvering the cannula guide body 28 with the slot 30, and may be used to lock the cannula guide body 28 into position.

The second bracket 26 may be rotationally connected to the first bracket 24. In one non-limiting embodiment, a knob 34 rotationally connects the second bracket 26 to the first bracket 24. The knob 34 may be secured in place by a keeper ring 35 (see FIG. 2B). The knob 34 is twisted in a first direction D1 to lock the positioning of the second bracket 26 relative to the first bracket 24, or is twisted in a second direction D2 to enable rotation of the second bracket 26 relative to the first bracket 24. In one non-limiting embodiment, the second bracket 26 is rotatable relative to the first bracket 24 over a range that extends from one side of the first bracket 24 to an opposite side of the first bracket 24.

Figure 8:
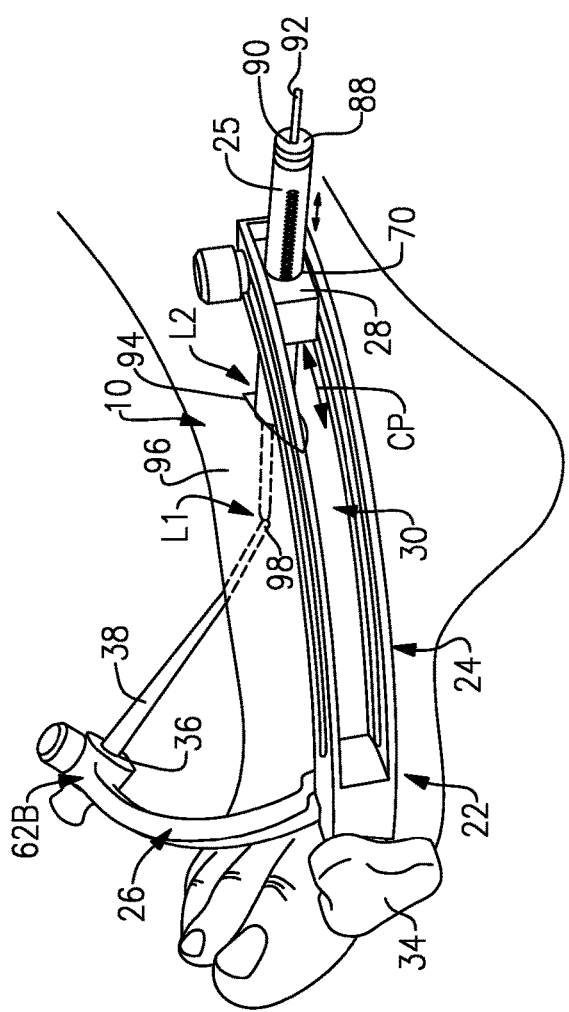
FIG. 8 schematically illustrates a method of using a targeting guide assembly to accurately position a surgical instrument within a joint.
Figure 9A:
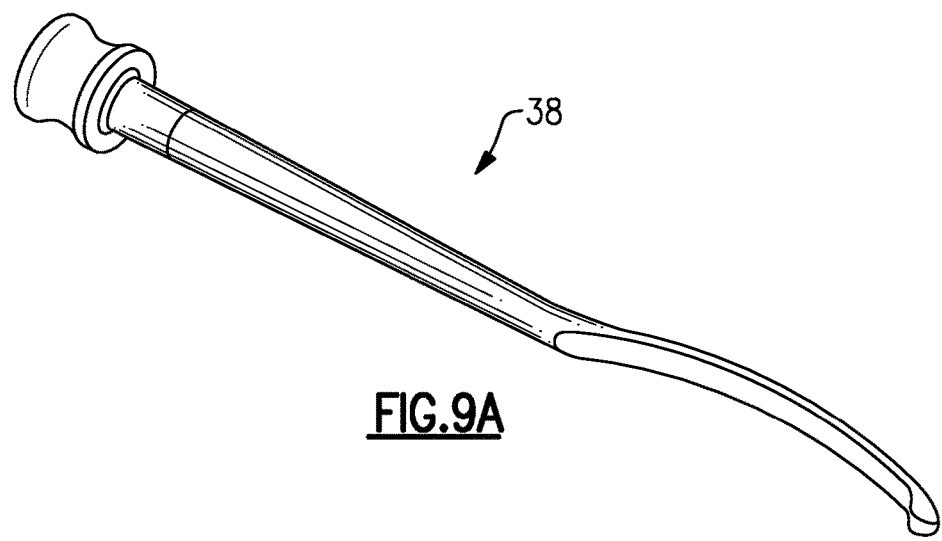
FIGS. 9A and 9B illustrate exemplary indicator probes for use with a targeting guide assembly.
Figure 9B:
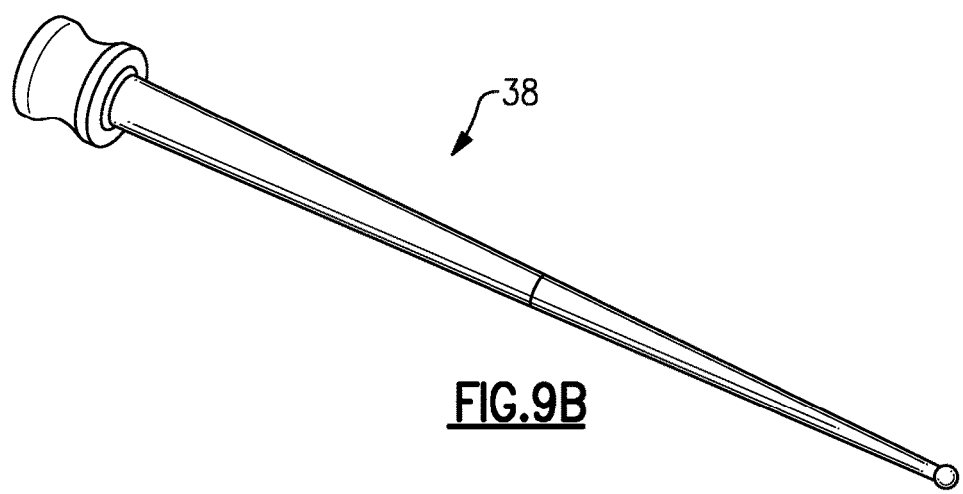
Figure 10:
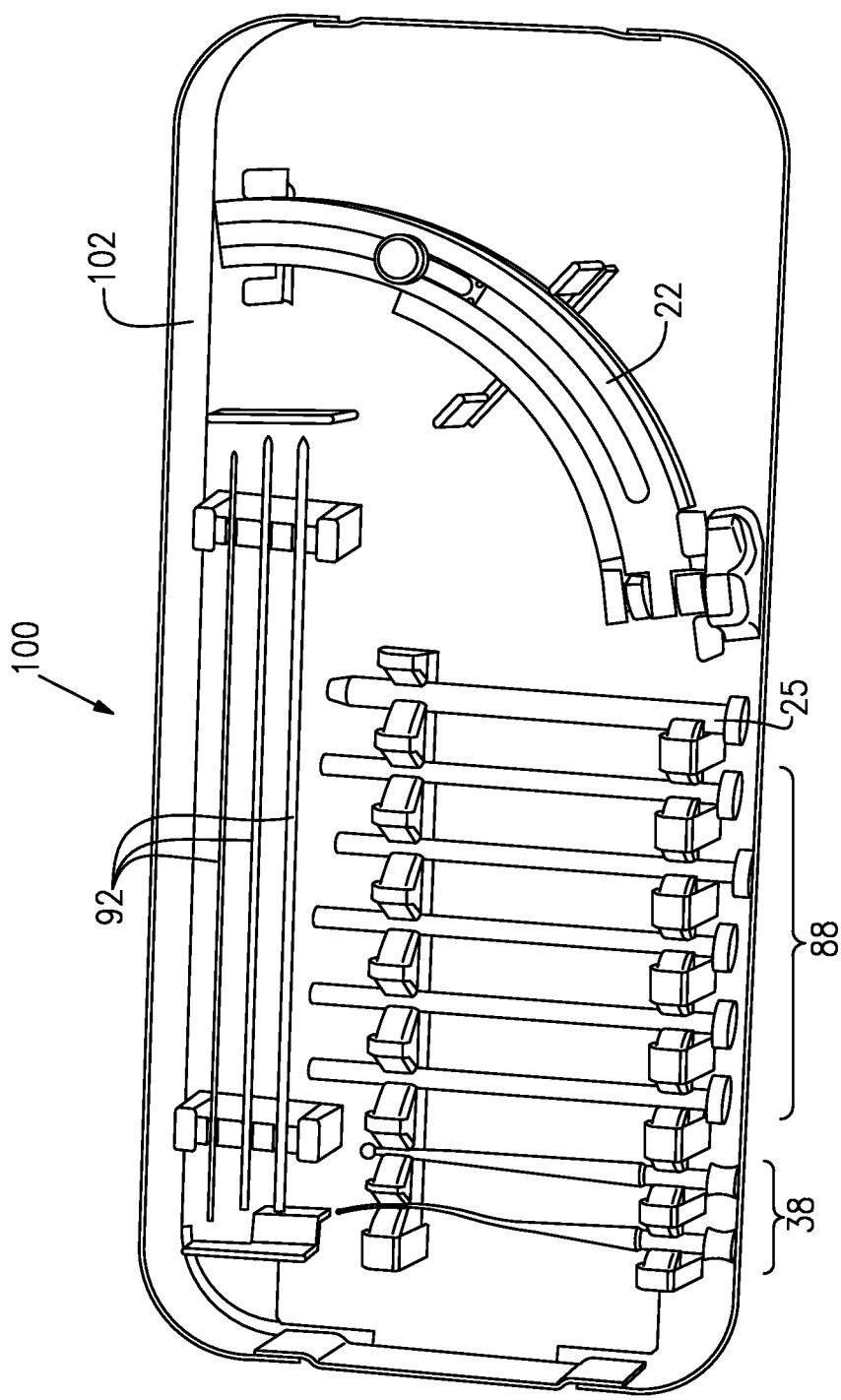
FIG. 10 illustrates a surgical kit that includes a targeting guide assembly and various other surgical instruments.

At an opposite end from its connection with the first bracket 24, the second bracket 26 includes a bore 36 sized to accommodate an indicator probe (identified using reference feature 38 in FIGS. 8-10). A knob 40 may be used to lock or release the indicator probe 38 for sliding movement within the bore 36. The knob 40 is received within an opening 42 that is transverse to the bore 36.

Figure 3A:
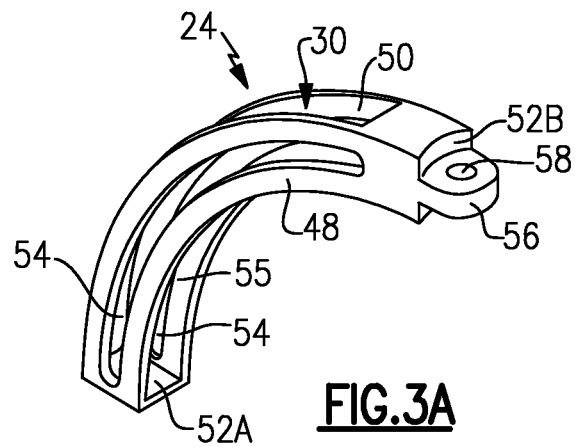
FIGS. 3A and 3B illustrate a first bracket of a targeting guide assembly.
Figure 3B:
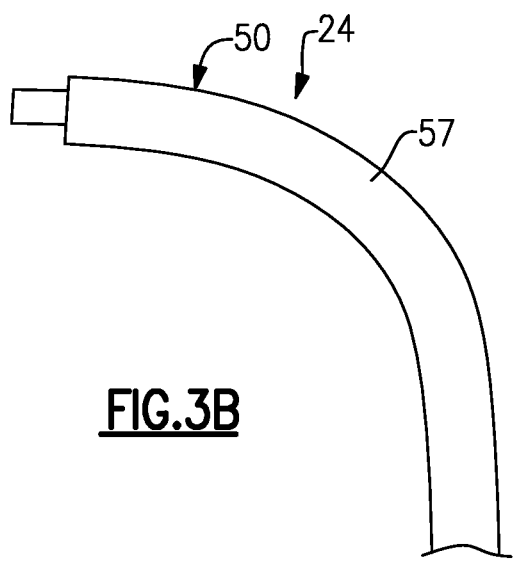

FIGS. 3A and 3B, with continued reference to FIGS. 2A and 2B, further illustrate the first bracket 24 of the targeting guide assembly 22. The first bracket 24 includes a curved body that includes a first arm 48 and a second arm 50 extending between opposing end walls 52A, 52B. The first arm 48 and the second arm 50 are spaced apart from one another to establish the slot 30. Tracks 54 of the slot 30 may be may be formed in both the first arm 48 and the second arm 50 for receiving and guiding the cannula guide body 28. In one non-limiting embodiment, the track 54 of the first arm 48 extends completely through the first arm 48. In another non-limiting embodiment, the track 54 of the second arm 50 is formed on an internal wall 55 of the second arm 50 and does not protrude through an external surface 57 of the second arm 50 (see FIG. 3B).

A mounting tab 56 protrudes from the end wall 52B and is configured to mate with a portion of the second bracket 26. The mounting tab 56 includes a bore 58 for receiving the knob 34 of the targeting guide assembly 22 to movably connect the first bracket 24 and the second bracket 26 together.

Figure 4A:
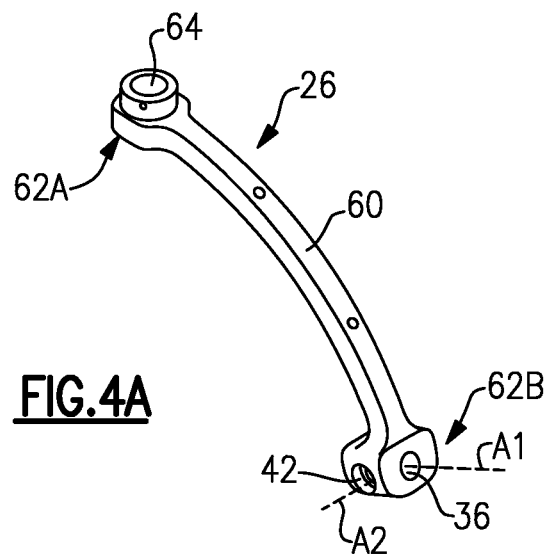
FIGS. 4A and 4B illustrate a second bracket of a targeting guide assembly.
Figure 4B:
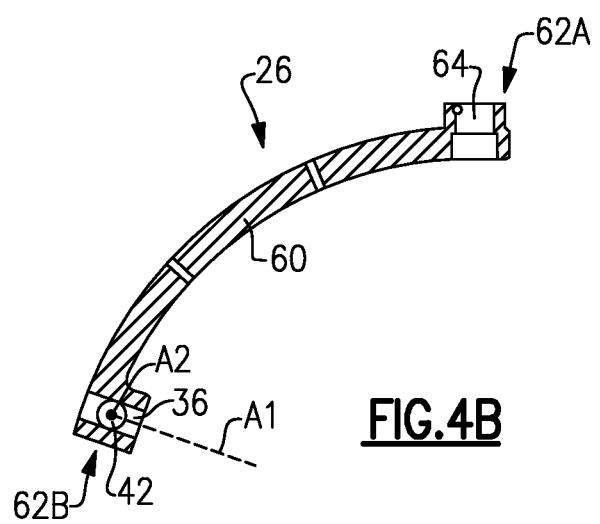
Figure 5A:
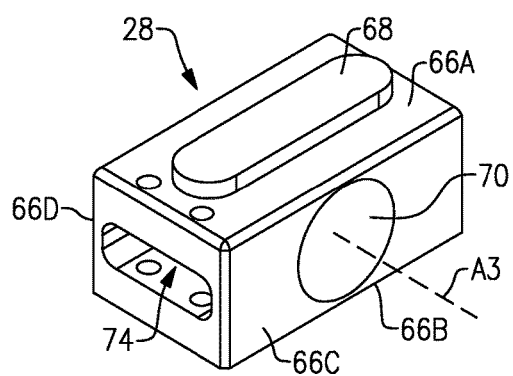
FIGS. 5A, 5B, 5C and 5D illustrate a cannula guide body of a targeting guide assembly.
Figure 5B:
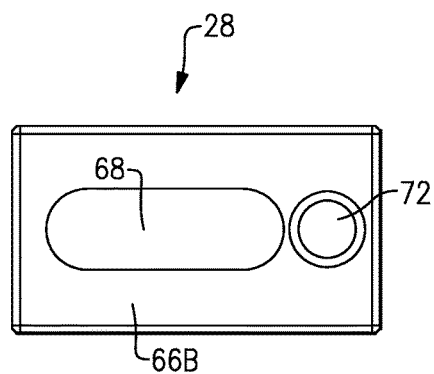
Figure 5C:
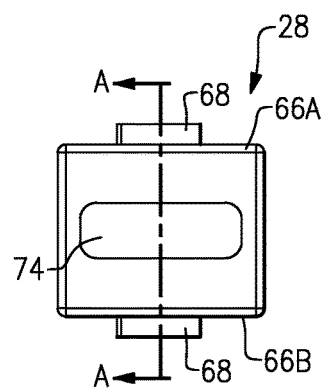
Figure 5D:
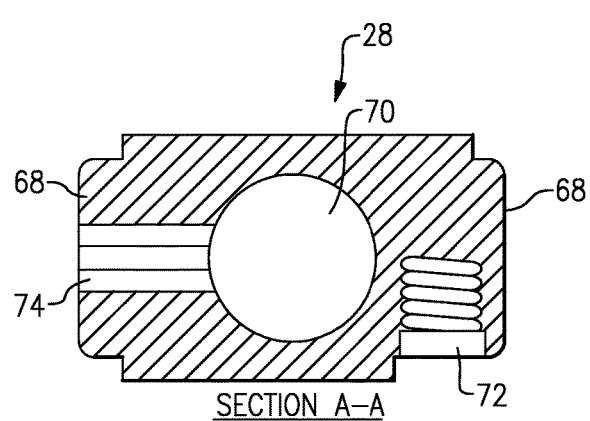

FIGS. 4A and 4B, with continued reference to FIGS. 2A and 2B, further illustrate the second bracket 26 of the targeting guide assembly 22. The second bracket 26 includes a curved body 60 that extends between opposing lugs 62A, 62B. The lug 62A is configured to abut against the mounting tab 56 of the first bracket 24 for rotatably attaching the second bracket 26 to the first bracket 24. The lug 62A includes a bore 64 for receiving the knob 34 of the targeting guide assembly 22.

The lug 62B includes the bore 36 for receiving an indicator probe 38 (see FIGS. 8-10) and the opening 42 for receiving the knob 40. The bore 36 extends through the lug 62B along a first axis A1, and the opening 42 extends into communication with the bore 36 along a second axis A2. In one non-limiting embodiment, the first axis A1 is perpendicular to the second axis A2.

FIGS. 5A, 5B, 5C and 5D, with continued reference to FIGS. 2A and 2B, further illustrate the cannula guide body 28 of the targeting guide assembly 22. The cannula guide body 28 is configured to move within the slot 30 of the first bracket 24. Therefore, the cannula guide body 28 may move along the curvilinear path established by the curvature of the first bracket 24.

The exemplary cannula guide body 28 may include a plurality of walls 66. In one non-limiting embodiment, the cannula guide body 28 includes a rectangular shape. Other shapes are also contemplated. A boss 68 extends from two opposing walls 66A, 66B of the exemplary cannula guide body 28. Once mounted within the targeting guide assembly 22, the bosses 68 protrude outwardly into the tracks 54 of the slot 30 of the first bracket 24 to guide the movement of the cannula guide body 28 within the slot 30.

Figure 7:
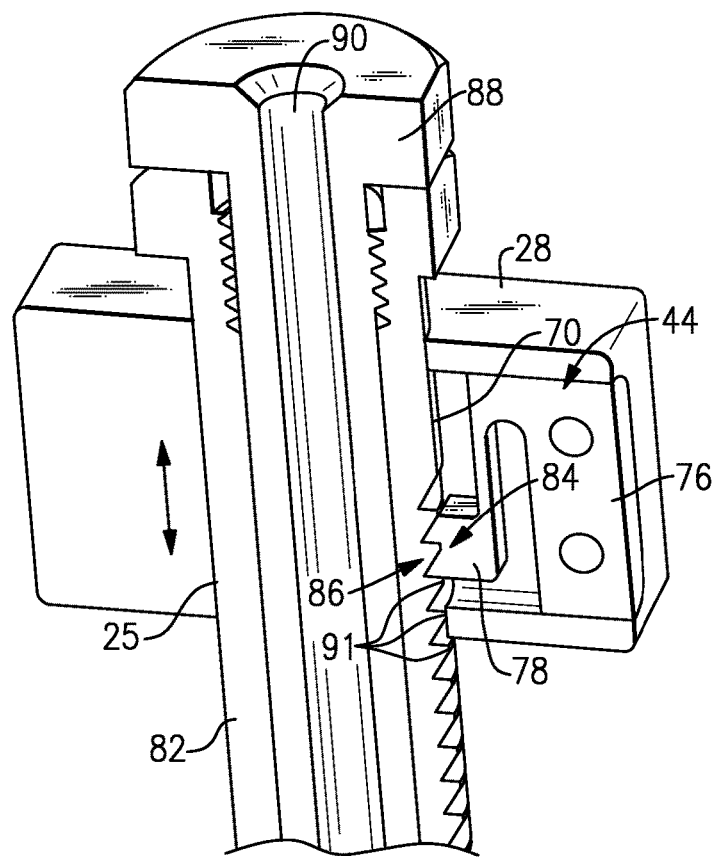
FIG. 7 illustrates a cannula and cannula sleeve of a targeting guide assembly.

The cannula guide body 28 may additionally include a bore 70 sized and shaped to receive a cannula (see, for example, reference feature 25 of FIGS. 7 and 8). The bore 70 may extend along an axis A3 between opposing walls 66C, 66D of the cannula guide body 28. In one non-limiting embodiment, the axis A3 is transverse to the direction of extension of each boss 68. A threaded opening 72 is formed in the cannula guide body 28 for receiving the guide knob 32, and a recessed opening 74 is formed in the cannula guide body 28 for receiving the ratchet 44. The recessed opening 74 opens into the bore 70.

Figure 6:
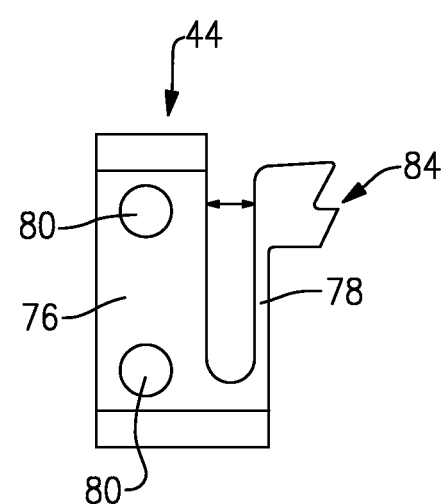
FIG. 6 illustrates a ratchet of a targeting guide assembly.

The ratchet 44 of the cannula guide body 28 is further illustrated in FIG. 6. The ratchet 44 may include a mounting portion 76 and a ratcheting leg 78 flexibly extending from the mounting portion 76. The mounting portion 76 includes openings 80 for securing the ratchet 44 within the recessed opening 74 using pins 46 (see FIG. 2B). The ratcheting leg 78 may be generally L-shaped and may include a first engagement feature 84 configured to engage mating features of another component of the targeting guide assembly 22, as further discussed below.

Referring now to FIG. 7, the ratcheting leg 78 of the ratchet 44 may flex in a direction toward or away from the mounting portion 76 to engage an outer surface 82 of a cannula 25 that is received through the bore 70 of the cannula guide body 28. For example, the first engagement feature 84 of the ratcheting leg 78 may articulate relative to a second engagement feature 86 of the cannula 25. In one non-limiting embodiment, the first engagement feature 84 is a recess and the second engagement feature 86 includes one or more teeth 91 that protrude from the outer surface 82 of the cannula 25. An opposite configuration is also contemplated in which the first engagement feature 84 is the male feature and the second engagement feature 86 is the female feature. The cannula 25 may be moved within the cannula guide body 28 by sliding the cannula within the bore 70 by applying a force to the cannula 25 in a manner that causes the first engagement feature 84 of the ratcheting leg 78 to move into and out of engagement with the second engagement feature 86 of the cannula 25. In this way, the cannula 25 can be ratcheted up or down relative to the cannula guide body 28 to achieve a desired depth relative to the joint.

The cannula 25 is hollow and therefore may receive a cannula sleeve 88. In one non-limiting embodiment, the cannula sleeve 88 screws into engagement with the cannula 25. The cannula sleeve 88 includes one or more openings 90 having an appropriate diameter for passing a surgical instrument, such as a guidewire, through the cannula sleeve 88 and into a joint. Cannula sleeves 88 having different sized openings 90 may be interchangeably received within the cannula 25. In addition, the cannula sleeve 88 may include multiple openings 90 (2, 3, 4, etc.) for passing multiple parallel guidewires. Different configurations of cannula sleeves 88 can be provided to provide different guidewire passing options.

FIG. 8 schematically illustrates an exemplary surgical technique for preparing the joint 10 for performing a surgical procedure using the targeting guide assembly 22 described above and illustrated throughout FIGS. 1-7. In one non-limiting embodiment, the surgical technique is an arthroscopic technique. However, the targeting guide assembly 22 could also be used during open procedures to accurately position a surgical instrument. In addition, the surgical technique described below could include a greater or fewer number of surgical steps, and these steps could be performed in any order, within the scope of this disclosure.

The surgical technique may begin by assembling the targeting guide assembly 22. Assembly includes one or more of the steps of inserting the cannula 25 through the bore 70 of the cannula guide body 28, inserting a properly sized cannula sleeve 88 into the cannula 25, and inserting an indicator probe 38 into the bore 36 of the lug 62B of the second bracket 26. The indicator probe 38 may be selected based on the type of joint being operated on. For example, if an ankle joint is being repaired, an indicator probe 38 specifically designed for the talar dome could be used (see, for example, FIG. 9A). In other joints or locations, a standard indicator probe 38 could alternatively be used (see, for example, FIG. 9B).

Next, the indicator probe 38 is positioned at a first location L1 of the joint 10. The indicator probe 38 may be inserted through an arthroscopic portal (not shown) and may be directed to the first location L1 under direct arthroscopic visualization. Selection of the first location L1 could depend on the type of procedure being performed and surgeon preference, among other factors. During this step, the knob 34 is loosened to allow the second bracket 26 to move relative to the first bracket 24 so the indicator probe 38 can be positioned at the ideal location of the joint 10 for achieving a proper trajectory of a guidewire 92. Once the indicator probe 38 has been positioned at the desired first location L1, the knob 34 is turned clockwise to lock movement of the second bracket 26 relative to the first bracket 24.

A small incision 94 can then be made through the skin 96 of the joint 10. The incision 94 marks the entry point for insertion of the cannula 25 and attached cannula sleeve 88 into the joint 10. The cannula guide body 28 may be moved along a curvilinear path CP defined by the slot 30 during positioning of the cannula 25 and may be locked into place using the guide knob 32 once a desired positioning is achieved. Once inserted, the cannula 25 is ratcheted into place at a desired second location L2 of the joint 10, such as directly against soft tissue or bone. Direct arthroscopic visualization can then be used to reconfirm proper placement of the indicator probe 38 and to confirm proper positioning of the cannula 25.

Once correct placement of both the indicator probe 38 and the cannula 25 at their respective first location L1 and second location L2 has been confirmed, a guidewire 92 having a desired diameter is inserted through the opening 90 of the cannula sleeve 88 and into the joint 10. In one non-limiting embodiment, the guidewire 92 is a K-wire. The guidewire 92 may be inserted through the cannula sleeve 88 and into the joint 10 using a surgical tool, such as a pin driver (not shown). Using arthroscopic visualization, the guidewire 92 is advanced along a desired trajectory until it contacts a tip 98 of the indicator probe 38. The targeting guide assembly 22, including the cannula 25 and cannula sleeve 88, may then be removed, leaving only the guidewire 92 in place within the joint 10.

With the guidewire 92 now accurately positioned, various additional surgical procedures can be performed on the joint 10. For example, by way of non-limiting examples, the guidewire 92 can be used to perform retrograde drilling within the joint 10 by drilling over the guidewire 92 with a cannulated drill bit or in preparation for the placement of cannulated screws within the joint 10. In another non-limiting embodiment, a cannulated drill is inserted over the guidewire 92 and drilled into the joint to remove a lesion.

FIG. 10 illustrates a surgical kit 100. The surgical kit 100 may include multiple surgical tools that can be used for accurate and repeatable guidewire placement within a joint. In one non-limiting embodiment, the surgical kit includes a targeting guide assembly 22, a plurality of cannula sleeves 88 having differently sized guidewire openings, multiple indicator probes 38, and/or a plurality of different sized guidewires 92. Each of these tools can be housed within a tray 102. Other surgical tools could additionally be part of the surgical kit 100.

The targeting guide assembly of this disclosure provides added variability to achieve simple and reproducible guidewire placement. The articulating and circumferentially movable cannula allows a surgeon to place the targeting guide assembly in the exact location necessary for passing a guidewire along a desired trajectory into a joint.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:
1. A targeting guide assembly, comprising:
a first bracket;
a second bracket rotatable relative to said first bracket;
a cannula guide body movable along a curvilinear path within a slot formed in said first bracket, wherein the slot extends between a first arm and a second arm of the first bracket, the slot including a track formed in the first arm, and the track is configured to guide movement of the cannula guide body along the curvilinear path;
a cannula received within a bore of said cannula guide body; and
a cannula sleeve received within said cannula.

2. The assembly as recited in claim 1, comprising a knob that rotatably connects said second bracket to said first bracket.

3. The assembly as recited in claim 1, wherein said cannula guide body includes a boss that extends into said track.

4. The assembly as recited in claim 1, comprising a knob mounted to said cannula guide body, said knob protruding outwardly from said slot.

5. The assembly as recited in claim 1, comprising a guidewire received through said cannula sleeve.

6. The assembly as recited in claim 1, comprising a ratchet received within a recessed opening of said cannula guide body.

7. The assembly as recited in claim 6, wherein said ratchet includes a first engagement feature adapted to engage a second engagement feature of a cannula received within said cannula guide body.

8. The assembly as recited in claim 7, wherein one of said first engagement feature and said second engagement feature is a recess and the other of said first engagement feature and said second engagement feature is a tooth.

9. The assembly as recited in claim 1, comprising an indicator probe received through a bore of said second bracket.

10. The assembly as recited in claim 9, comprising a knob configured to lock a positioning of said indicator probe within said bore.

11. The assembly as recited in claim 1, wherein said cannula is axially between said first arm and said second arm of said first bracket.

12. The assembly as recited in claim 1, wherein said track extends completely through said first arm, and comprising a second track formed in said second arm without extending completely through said second arm.

13. The assembly as recited in claim 1, wherein said cannula sleeve includes a first opening having a first diameter that is smaller than a second diameter of a second opening of said cannula.

14. The assembly as recited in claim 1, wherein said cannula sleeve includes a plurality of openings, and each of said plurality of openings is sized to receive a guidewire.

15. A surgical method, comprising:
    positioning an indicator probe of a targeting guide assembly at a first location of a joint, wherein the indicator probe is inserted through a first bore of the targeting guide assembly;
    positioning a cannula of the targeting guide assembly at a second location relative to the joint such that the cannula is aligned to establish a desired trajectory toward the indicator probe, wherein positioning the cannula includes inserting the cannula through a second bore of a cannula guide body and then moving the cannula guide body along a curvilinear path established by a slot of the targeting guide assembly,
    wherein, once received within the second bore, the cannula extends through the slot at a location that is axially between a first arm and a second arm of a first bracket of the targeting guide assembly; and
    inserting a surgical instrument through the cannula along the desired trajectory.

16. The method as recited in claim 15, wherein moving the cannula guide body includes sliding the cannula guide body along the curvilinear path.

17. The method as recited in claim 15, wherein positioning the indicator probe includes moving a second bracket of the targeting guide assembly relative to the first bracket.

18. The method as recited in claim 15, wherein positioning the cannula includes ratcheting the cannula up or down relative to the cannula guide body.

19. The method as recited in claim 15, wherein the surgical instrument is a guidewire and the inserting includes moving the guidewire along the desired trajectory until it contacts a tip of the indicator probe.

20. The method as recited in claim 15, wherein the surgical instrument is a guidewire and the method further comprises:
    removing the targeting guide assembly from the joint while leaving the guidewire in place within the joint; and
    drilling over the guidewire with a cannulated drill bit.

21. A targeting guide assembly, comprising:
    a first bracket including a first curved body;
    a second bracket including a second curved body;
    a knob rotationally connecting the first bracket and the second bracket, wherein the knob is configured to twist in a first direction to lock the second bracket relative to the first bracket and in a second direction to enable the second bracket to rotate relative to the first bracket;
    a cannula guide body mounted within a slot of the first bracket, wherein the cannula guide body is movable along a curvilinear path established by the slot;
    a cannula received through a first bore of the cannula guide body;
    a cannula sleeve received within the cannula;
    a guidewire received through the cannula sleeve; and
    an indicator probe received through a second bore of the second bracket.

* * * * *